Aug 6, 1974 D. L. ARMSTRONG Plant Pat. 3,584
ROSE PLANT
Filed Feb. 16, 1973
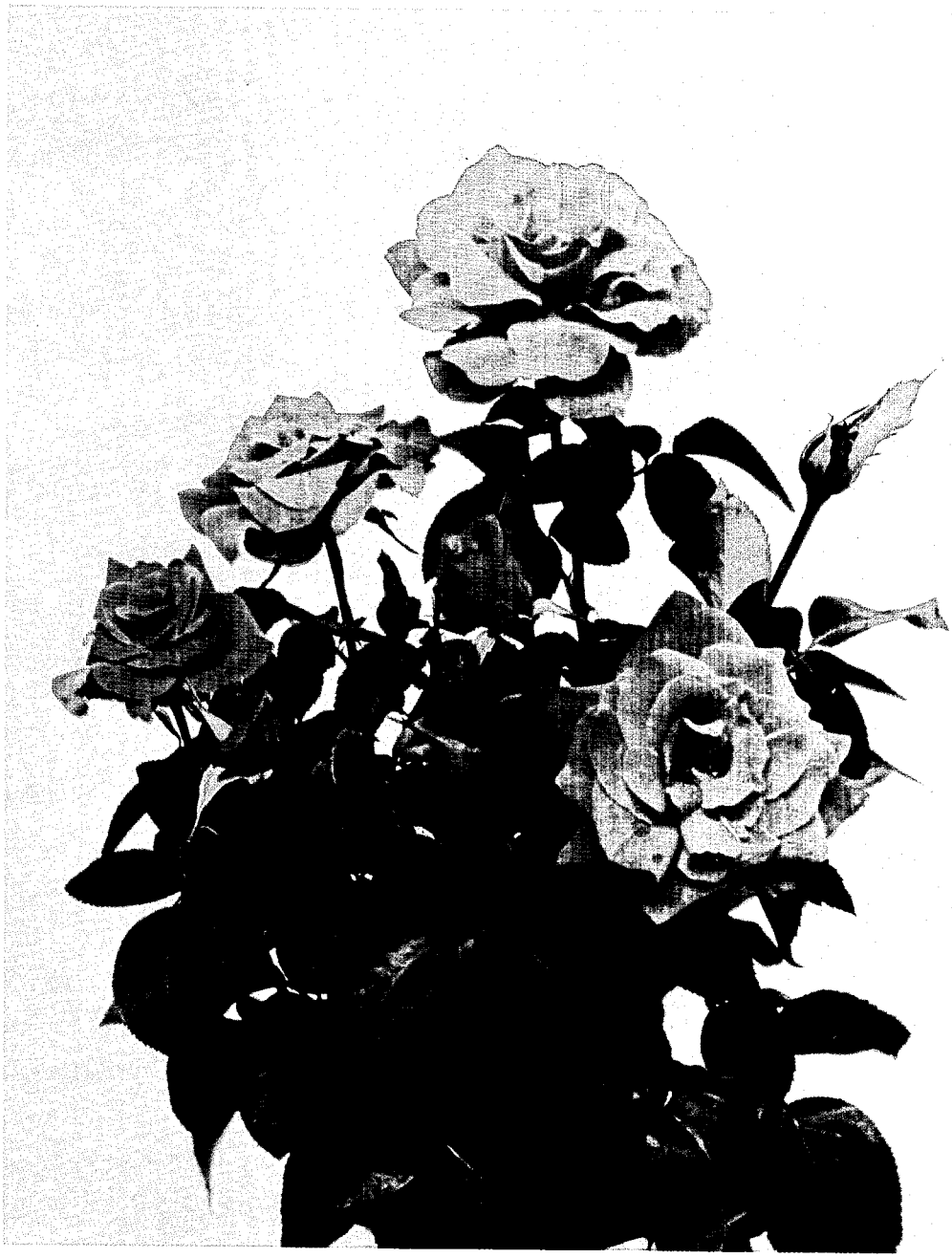

United States Patent Office

Plant Pat. 3,584
Patented Aug. 6, 1974

3,584
ROSE PLANT

David L. Armstrong, Orange, Calif., assignor to
Armstrong Nurseries, Inc., Ontario, Calif.
Filed Feb. 16, 1973, Ser. No. 333,137
Int. Cl. A01h 5/00
U.S. Cl. Plt.—20 1 Claim

ABSTRACT OF THE DISCLOSURE

A rose plant of the hybrid tea class grown as an outdoor seedling, primarily for garden decoration. The plant is bushy, upright-spreading, heavily branched, and with an abundance of medium size, semi-glossy foliage, the leaflets having irregularly serrated margins. From opening bud to final petal fall the blooms maintain a strong red color, with very little change in shade.

The flowers are usually borne singly, but may come as many as five on a steam, the blooms opening to from 3¾ to 5 inches, and being cupped to high-centered, with double pentalage and moderate sweetbriar fragrance.

This invention relates to a hybrid tea rose not yet fully tested for hardiness, which is an outdoor seedling of bush form best adapted for garden decoration. It was discovered and has been asexually reproduced by David L. Armstrong at Ontaria, Calif. It holds its characteristics through succeeding propagations by budding.

Its flowers are borne usually singly, but are sometimes ranging from 3 to 5 on the stem. The stems are strong, of medium length, and the quantity of bloom is free to abundant, being nearly continuous throughout the growing season. The fragrance is a moderate sweetbriar odor.

The seed parent, an unnamed and undisseminated seedling, is not presently available for comparison with the new cultivar. However, compared with the parents of that seedling, which itself resulted from a cross of Charlotte Armstrong × Red Jacket, flowers of the new rose display a more deep-seated red than Charlotte Armstrong and have more petals than Red Jacket.

The pollen parent likewise is an unnamed and undisseminated seedling, resulting from a cross of Roundelay × Chrysler, and is no longer available for comparison. Compared to its paternal grandparents, however, the new cultivar has fewer petals in its flowers than either Roundelay or Chrysler.

The accompanying drawing illustrates the plant in color and shows the flowing thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length, average to heavy in caliper, and erect, with some stipitate glands and some very small prickles. Its color is near Strong Yellow Green, 5GY6/8, lightly overlaid with near Dark Red, 5R3/7, on the side exposed to sunlight.

*Before the calyx breaks,* its size is medium, for its class. In form, it is medium length, ovoid, and usually having slender foliaceous parts extending beyond the tip of the bud equal to from ¼ to ½, or more, of its length. As the calyx breaks, its color is between black and Dark Red, 2.5R3/7.

Margins of alternate sepals are lined with a fine, wooly tomentum, while margins of others have stipitate glands and a few small foliaceous parts. The sepals have narrow foliaceous parts extending out beyond the tip of the bud from ¼ to ½, or more, of the bud length.

As the first petal opens, it is average in size, for the class, medium length to long, and from pointed to urn-shaped. On the outer surface the color ranges between blacklish red and near Moderate Red, 2.5R4/10, with a very small area at the base which is near Brilliant Yellow Green, 2.5GY9/8. The inner surface ranges from blackish red to a color between Dark Red, 5R3/7, and Strong Red, 5R4/12, with a very small area at the base near Brilliant Greenish Yellow, 10Y9/9.

The bud opens up well, and is not retarded or prevented from opening by cold, hot, wet, or dry weather.

BLOOM

The size of the bloom when fully open is average, for its class, being from 3¾ inches to 5 inches in diameter. The petalage is double, with from 23 to 35 petals, plus 4 to 10 petaloids arranged regularly (in August). The bloom is high centered at first, becoming later from cupped to high centered. The petals remain cupped at first, with tips reflexed outward, becoming later at maturity more loosely cupped, with tips reflexed outward.

The petals are of medium thickness and moderately leathery, with inside slightly satiny to velvety, while the outside is slightly shiny to satiny. The outside petals are nearly round, the intermediate petals nearly round to broadly obovate, while the inside petals are from nearly round to highly irregular, usually having one notch. The colors may be modified by being bordered or margined, blotched, shaded and/or washed with other colors.

The paragraphs immediately following describe color values observed in a flower *newly opened* in the month of August. The plant had been grown outdoors, in Ontario, Calif.

The outer surface of the outside petal was near Moderate Red, 2.5R4/10, with a small area at the base near Brilliant Greenish Yellow, 7.5Y9/8. The inner surface of the outside petal was between Dark Red, 2.5R3/7, and Strong Red, 5R4/12, and also carried a small area at the base near Brilliant Greenish Yellow, 7.5Y9/8.

The outer surface of the intermediate petal was between Strong Red, 2.5R5/12, and Moderate Red, 2.5R4/10, with a small portion at the base near Brilliant Greenish Yellow, 7.5Y9/8. The inner surface of the intermediate petal corresponded to the outer surface, in color.

The outer and inner surfaces of the inner petal are the same in color, being between Strong Red, 2.5R5/12, and Moderate Red, 2.5R4/10, with a white streak sometimes appearing along the mid-rib.

The paragraphs immediately following describe the color values observed in a bloom which had been *open for three days* in the month of August. The plant had been grown outdoors, in Ontario, Calif.

The outer surface of the outside petal was near Strong Purplish Red, 10RP4/12. The inner surface of the outside petal was also near Strong Purplish Red, 10RP4/12, but became nearer to Dark Red, 2.5R3/7, along the margins.

The outer surface of the inside petal was between Strong Purplish Red, 10RP5/12, and Strong Purplish Red, 10RP4/12. The inner surface of the inside petal was near Strong Purplish Red, 10RP4/12.

The general color effect of the newly opened flower was a color more vivid than but between Strong Red, 5R4/12, and Moderate Red, 2.5R4/10. After being three days open, the bloom had the general color effect of near Strong Purplish Red, 10RP4/12.

The petals drop off cleanly, and are not particularly affected by cold, hot, wet, or dry weather.

The flower on the bush in the garden persists for from 3 to 5 days in the month of June. Cut roses grown outdoors and kept at living-room temperatures will last from 3 to 5 days in the month of August.

REPRODUCTIVE ORGANS

Stamens: There are many stamens, arranged regularly about the pistils, a few being mixed with petaloids or tucked in the calyx.

Filaments: Short to medium-length, being from ¼" to ⅜" in length. The color is near Brilliant Yellow, 5Y9/9, at the base, becoming near Strong Pink, 2.5R7/8. Most are with anthers.

Anthers: Anthers are of medium size, and all open approximately at once. On the upper side, the color is near Pale Orange Yellow, 7.5YR9/4, with the margins being near Strong Orange Yellow, 7.5YR7/11. The color on the under side is near Pale Orange Yellow, 7.5YR9/4.

Pollen: Pollen is from moderate to abundant, and near Strong Orange Yellow, 7.5YR7/11, in color.

Pistils: There are many pistils, numbering approximately 185.

Styles: The styles are uneven, of average length and caliper, and somewhat loosely bunched. Beneath the stigma, the color is near Moderate Red, 2.5R4/10.

Stigma: Near Pale Orange Yellow, 7.5YR9/4.

Ovaries: Usually, most of the ovaries are enclosed in the calyx, with some protruding therefrom.

Hips: Average length; globular; smooth; walls thick, fleshy; color (⅓ to ½ mature)—between Strong Yellow Green, 2.5GY6/8, and Moderate Yellow Green, 2.5GY5/5.

Sepals: Permanent; medium-length to long; spear-shaped, recurved slightly. Color inside: (⅓ to ½ ripe hip) generally between Strong Red, 2.5R5/12, and Moderate Red, 2.5R4/10, heavily overlaid with fine wooly tomentum. Color outside: (⅓ to ½ ripe hip) between Strong Yellow Green, 2.5GY6/8, and Moderate Yellow Green, 2.5GY5/5.

Seeds: Average number to many; usually medium size, and 3 to 28 in number.

FOLIAGE

The leaves are compound, and usually have from 3 to 7 leaflets. They are abundant, medium in size, moderately heavy and semi-glossy. The leaflets are ovate, with apex mucronate, base obtuse, and margin irregularly serrate.

On its upper surface the *mature leaf* is between Moderate Olive Green, 5GY4/3, and Grayish Olive Green, 5GY3/2, while the under surface is grayer than a color somewhat between Strong Yellow Green, 7.5GY6/8, and Moderate Yellow Green, 7.5GY5/7.

The *young foliage* is near Strong Yellow Green, 2.5GY6/8, heavily overlaid with near Dark Red, 5R3/7, on both its upper and under surfaces.

The *rachis* is from average size to heavy, its upper side being grooved and with some stipitate glands on the edges. The under side is moderately prickly, with some stipitate glands.

The *stipules* are medium-length, moderately narrow, and with narrow long points turning out at an angle of usually less than 90°.

The plant diplays an average resistance to mildew, when compared with other varieties now in commerce grown under comparable conditions.

In habit of growth, the plant is bushy, upright—spreading, much branched, and moderately vigorous. The canes are from medium to heavy caliper.

The *main stems* are between Moderate Yellow Green, 2.5GY5/5, and Moderate Olive Green, 2.5GY4/3, becoming streaked with gray to Strong Yellowish Brown, 7.5YR5/7. There are several moderately short to medium-length large prickles which are hooked slightly downward, and have moderately short to medium-length, moderately narrow bases. There are from none to few small prickles, but both the large and small prickles are between gray and Strong Brown, 5YR4/5. There are no hairs.

The *branches* are between Moderate Yellow Green, 2.5GY5/5, and Moderate Olive Green, 2.5GY4/3. There are several large prickles which are medium-length, hooked downward, with moderately short, moderately narrow bases. There are few small prickles, but both large and small prickles are between Strong Brown, 5YR4/5, and Moderate Brown, 5YR3/3, or graying at the tips. There are no hairs, but there may be several stipitate glands.

The *new shoots* are between Strong Yellow Green, 5GY6/8, and Moderate Yellow Green, 2.5GY5/5, lightly to heavily overlaid with near Dark Red, 5R3/7, in area exposed to the sun. There are from few to several large prickles, these being medium-length to long, hooked slightly downward, with medium-length narrow bases. Their color is near Dark Greenish Yellow, 10Y6/7, lightly to heavily overlaid with near Dark Red, 2.5R3/7. There are a few small prickles, from few to several stipitate glands, but no hairs.

I claim:

1. A rose plant of the hybrid tea class, substantially as shown and described, and having a plurality of combinations of characteristics, including a bushy, upright-spreading much branched habit of growth, with abundant semi-glossy foliage comprising leaflets with irregularly serrate margins, and stems bearing several large prickles and few if any small ones; long pointed to urn-shaped buds, opening to cupped to high-centered blooms with 23 to 35 petals, 4 to 10 petaloids, producing a strong red overall color effect which persists almost unchanged until petal fall; blooms having sweetbriar fragrance, and being usually borne singly but occasionally as many as five on a single stem, both peduncles ranging from average to heavy caliper with some stipitate glands and very small prickles.

No references cited.

ROBERT E. BAGWILL, Primary Examiner

UNITED STATES PATENT OFFICE

CERTIFICATE OF CORRECTION

Patent No. PP 3584 Dated August 6, 1974

Inventor(s) David L. Armstrong

It is certified that error appears in the above-identified patent and that said Letters Patent are hereby corrected as shown below:

Column 1, line 18 - "steam" should be --stem--

Column 1, line 27 - "Ontaria" should be --Ontario--

Column 1, line 48 - "flowing" should be --flowering--

Column 2, line 4 - "blacklish" should be --blackish--

Column 3, line 24 - after "7.5YR9/4" and before the period (.) insert --, in color--

Column 4, line 52 - "both" should be --with--

Signed and sealed this 1st day of April 1975.

(SEAL)
Attest:

RUTH C. MASON
Attesting Officer

C. MARSHALL DANN
Commissioner of Patents
and Trademarks